US00PP30545P2

(12) United States Plant Patent
Snijder

(10) Patent No.: US PP30,545 P2
(45) Date of Patent: May 28, 2019

(54) POINSETTIA PLANT NAMED 'EURZ0009'

(50) Latin Name: *Euphorbia pulcherrima*
Varietal Denomination: EURZ0009

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,905

(22) Filed: May 18, 2018

(30) Foreign Application Priority Data

Oct. 27, 2017 (QZ) ..... PBR 2017/2746

(51) Int. Cl.
*A01H 5/02* (2018.01)

(52) U.S. Cl.
USPC ..... Plt./307
CPC ..... *A01H 5/02* (2013.01)

(58) Field of Classification Search
USPC ..... Plt./307
CPC ..... A01H 5/0244
See application file for complete search history.

*Primary Examiner* — Kent L Bell
(74) *Attorney, Agent, or Firm* — Dale Skalla

(57) ABSTRACT

A new Poinsettia plant named 'EURZ0009' particularly distinguished by an intense dark red bract color, medium-large sized inflorescences with a large set of pronounced cyathia, compact vigor and a tight plant habit.

1 Drawing Sheet

Figure 1:
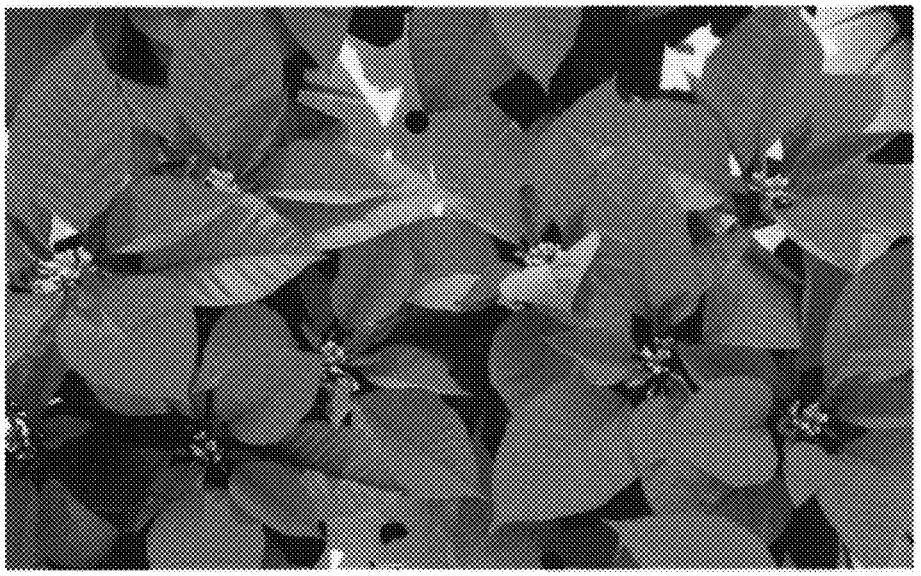

Latin name of the genus and species of the plant claimed: *Euphorbia pulcherrima.*

Varietal denomination: 'EURZ0009'.

BACKGROUND OF THE NEW PLANT

The present invention comprises a new Poinsettia, botanically known as *Euphorbia pulcherrima*, and hereinafter referred to by the variety name 'EURZ0009'.

'EURZ0009' is a product of a planned breeding program. The new cultivar has intense dark red bract color, medium-large inflorescences with a large set of pronounced cyathia compact vigor and a tight plant habit.

'EURZ0009' originates from a hybridization in a controlled breeding program made in September 2012 in a greenhouse in Enkhuizen, The Netherlands. The female parent was a plant of *E. pulcherrima* parentage, identified as 'SYEP22866' and described in U.S. Plant Pat. No. 22,554 with smaller bracts and more branches when compared to 'EURZ0009'.

The male parent was a plant of *E. pulcherrima* parentage, identified as 'NPCW10158' and described in U.S. Plant Pat. No. 22,580 with a more round compact plant shape when compared to 'EURZ0009'.

These plants were multiplied separately and examined during next fall-winter flowering for uniformity and stability of the new combination of characteristics.

The first act of asexual reproduction of 'EURZ0009' had been accomplished when shoot tip cuttings were used from the initial selection in late July 2013, rooted and cultivated.

More cuttings were used from the selected plant from July through December 2013 and grafted onto rootstocks of the variety 'Maren', in order to improve the branching ability. Shoot tip cuttings from successfully grafted stems were used in the summer of summer of 2014. They were rooted and cultivated as branched plants for a small trial in the fall and winter of 2014.

Horticultural examinations of plants grown from cuttings of the plant started in the fall to winter of 2014. Examinations continuing thereafter on a larger scale, have demonstrated that the combination of characteristics as herein disclosed for 'EURZ0009' are firmly fixed and are retained through successive generations of asexual reproduction.

BRIEF SUMMARY OF INVENTION

Horticultural examination of plants grown from cuttings of the plant initiated in July 2013, and continuing thereafter, has demonstrated that the combination of characteristics as herein disclosed for 'EURZ0009' are firmly fixed and are retained through successive generations of asexual reproduction.

'EURZ0009' has not been observed under all possible environmental conditions. The phenotype may vary significantly with variations in environment such as temperature, light intensity and day length.

A Plant Breeder's Right for this cultivar was applied for in the European Union on Oct. 27, 2017, No. 2017/2746. 'EURZ0009' has not been made publicly available prior to the effective filing date of this application, notwithstanding any disclosure that may have been made less than one year prior to the effective filing date of this application by the inventor or another who obtained 'EURZ0009' directly from the inventor.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

The accompanying photographic drawings show typical flower and foliage characteristics of 'EURZ0009' with colors being as true as possible with an illustration of this type. The photographic drawings show a flowering potted plant of the new variety.

Figure 2:
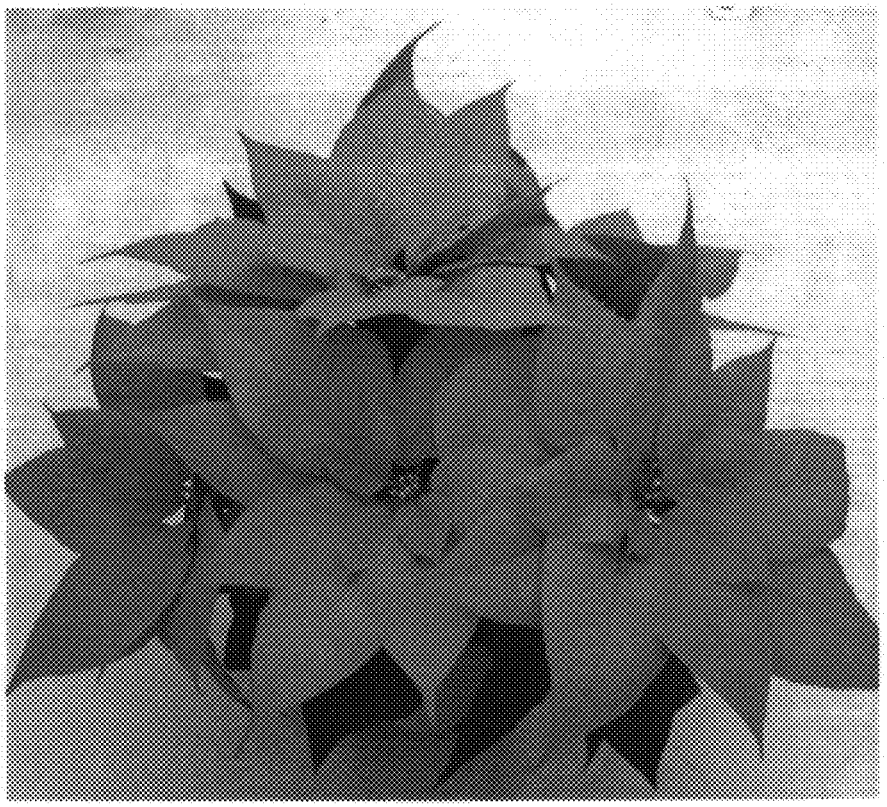

FIG. 1, taken on Nov. 15, 2016 shows a view of the bracts from the top of plant, on a plant about 20 weeks old;

FIG. 2, taken on Dec. 2, 2015, shows a side view of a 23 week old plant.

DETAILED BOTANICAL DESCRIPTION

The measurements were taken in Enkhuizen, the Netherlands in mid December 2017 on about 20 week old plants growing in a greenhouse. Culture of these plants had started in late July 2017 with planting rooted cuttings in 13 cm pots and terminal pinching about 2 weeks later. The plants were grown under natural day light in the fall (no black cloth to initiate earlier flowering) and at the moderately warm temperature of 18° C. for the bench heating.

Color references are made to The Royal Horticultural Society Colour Chart (R.H.S.) 2001.

TABLE 1

DIFFERENCES BETWEEN THE NEW VARIETY 'EURZ0009' AND A SIMILAR VARIETY

| | 'EURZ0009' | 'SYEP22866' (U.S. Plant Pat. No. 22,554) |
|---|---|---|
| Bract size: | Medium-large | Small-medium |
| Inflorescence shape: | Bowl-plate shape | Cup-bowl shape |

Plant:

*Form, growth and habit*.—Shrub, with the branches slanting upright, good branching.

*Plant height* (*inflorescence included*).—35-36.5 cm.

*Plant width*.—25-27 cm.

Roots:

*Number of days to initiate roots*.—18-20 days at about 24 degrees C.

*Number of days to produce a rooted cutting*.—24-26 days at 24 degrees C.

*Type*.—Fine, fibrous, free branching.

*Color*.—RHS N155B but whiter.

Foliage:

*Arrangement*.—Alternate, 7-9 leaves per branch.

*Immature, leaf color, upper surface*.—Approximately RHS 143A.

*Lower surface*.—RHS 144B.

*Mature, leaf color, upper surface*.—RHS 139A.

*Lower surface*.—RHS 137D.

*Length*.—10-11 cm.

*Width*.—8-9 cm.

*Shape*.—Ovate, with almost no lobes.

*Base shape*.—Truncate to obtuse.

*Apex shape*.—Acuminate.

*Margin*.—Entire; lobes, when present mostly rounded.

*Aspect*.—Leaf blades are horizontally or slightly downwards directed.

*Texture, upper surface*.—Smooth.

*Lower surface*.—Smooth, apart from the protruding veins.

*Color of veins, upper surface*.—RHS 53C or RHS 47B at the base, fading towards the leaf tip.

*Color of veins, lower surface*.—RHS 48A fading towards the leaf tip.

*Petiole color, upper surface*.—RHS 60B.

*Lower surface*.—RHS 53B.

*Length*.—Most often 7-8 cm.

*Diameter*.—0.2-0.3 cm.

*Aspect*.—Horizontally to slightly upward directed.

*Texture*.—Glabrous.

Stem:

*Quantity of main branches per plant*.—About 4-5.

*Color of stem*.—Mainly RHS 146A to RHS 146B; RHS 176B and RHS 182B at the upper third of the stems.

*Length of stem*.—25-28 cm.

*Diameter*.—0.6-0.8 cm.

*Length of internodes*.—2.5-4.5 cm.

*Texture*.—Glabrous.

*Color of peduncle*.—RHS 144B to RHS 144C.

*Length of peduncle*.—0.2-0.3 cm.

*Peduncle diameter*.—0.2 cm.

*Texture*.—Glabrous.

Inflorescence:

*Type*.—Terminal cyme with surrounding whorl of colored bracts.

*Flowering, botanically* (*opening of the stamen, shedding of pollen*).—Late November.

*Flowering, commercially* (*sufficiently colored bracts*).—Mid November.

*Flowering response time*.—About 7-8 weeks from equinox.

*Duration of flowering*.—Depends on light and environment, at least 4-6 weeks of 'shelf' life.

*Fragrance*.—Absent.

*Shape of inflorescence*.—Rosette-like whorl, star-shaped; bracts borne nearly horizontally to weakly funnel-shaped (slanting upright); tight center.

*Diameter of inflorescence*.—18-24 cm.

*Inflorescence, vertical diameter*.—3.5-4.5 cm.

*Number of completely colored bracts per inflorescence* (*sized over 2 cm*).—11-14.

*Single bract, shape*.—Ovate with relatively long, pointed tips, without or with weak lobes.

*Bract, apex*.—Acuminate.

*Bract, base*.—Weakly rounded.

*Single bract, length of blade*.—12 cm, younger bracts diminishing in size.

*Single bract, width of blade*.—6-8 cm.

*Bract color, upper side*.—Closest to RHS 46A.

*Bract color, lower side*.—Slightly more bluish than RHS 47A.

*Vein color, upper surface*.—Indistinct, similar as bract blade.

*Vein color, lower surface*.—Approximately RHS 48B.

*Texture*.—Weakly rugose, glabrous.

*Bract petiole color, upper surface*.—RHS 46A.

*Bract petiole color, lower surface*.—Approximately RHS 47A.

*Bract petiole, length*.—About 2.0 cm, shorter with younger bracts.

*Bract petiole diameter*.—0.2-0.3 cm.

Cyme (true inflorescence):

*Cyme, diameter*.—1.7-2.1 cm.

*Number of cyathia*.—5-13, borne in a tight cluster.

*Cyathium, shape*.—Ovate.

*Cyathium, diameter*.—0.4-0.6 cm.

*Cyathium, length*.—0.6-0.7 cm.

*Color*.—RHS 144A to RHS 144B, top is RHS 46B.

*Nectar cups*.—Usually one per cyathium.

*Nectur cup, width*.—0.4-0.5 cm.

*Nectar cup, color*.—Closest to RHS 17B.

Reproductive organs:

*Stamen* (*actually reduced male florets*).—Usually in a small bunch of 10-20 at the top of the cyathium.

*Shape*.—Strap-like.

*Filament length*.—0.2 cm.

*Filament color*.—RHS 46A to RHS 46B.

*Anther color*.—RHS 11A.

*Anther diameter*.—0.1 cm.

*Pollen quantity*.—Moderate (normal quantity).

*Pollen color*.—RHS 12A.

*Female flowers*.—Appear sparse in mid winter, as occurrence depends much on light intensity, appear (if at all) about 4 weeks later than the stamen, a single flower emerges from the top of the cyathium with a short pedicel.

*Style, length*.—0.2-0.3 cm.

*Stigma shape*.—Trifurcate, 6-lobed.

*Style and stigma color*.—RHS 46A to RHS 46B.

*Ovary shape*.—Obovate, 3 ovules.

*Ovary size*.—0.3-0.4 cm in diameter (probably larger in seasons or regions with higher light intensity).

*Ovary color*.—RHS 143A.

*Fertility/seed set*.—Has not been observed on this plant.

Disease/pest resistance: Disease/pest resistance has not been observed on this plant.

What is claimed is:

1. A new and distinct variety of Poinsettia plant named 'EURZ0009,' substantially as illustrated and described herein.

* * * * *